United States Patent [19]

Ronnett et al.

[11] Patent Number: 5,318,907

[45] Date of Patent: * Jun. 7, 1994

[54] PRIMARY CULTURE OF OLFACTORY NEURONS

[75] Inventors: Gabriele Ronnett, Baltimore; Lynda Hester, Towson; Solomon Snyder, Baltimore, all of Md.

[73] Assignee: The Johns Hopkins University, Baltimore, Md.

[*] Notice: The portion of the term of this patent subsequent to Jun. 8, 2010 has been disclaimed.

[21] Appl. No.: 957,021

[22] Filed: Oct. 6, 1992

Related U.S. Application Data

[62] Division of Ser. No. 633,513, Dec. 31, 1990, Pat. No. 5,217,893.

[51] Int. Cl.$^5$ ................................................ C12N 5/00
[52] U.S. Cl. ............................. 435/240.21; 435/240.1; 435/240.2; 435/240.243
[58] Field of Search ............ 435/240.1, 240.2, 240.21, 435/240

[56] References Cited

U.S. PATENT DOCUMENTS 4,963,489 10/1990 Naughton et al. ............... 435/240.1
5,217,893 6/1993 Ronnett et al. ................. 435/240.21

FOREIGN PATENT DOCUMENTS 0247881 12/1987 European Pat. Off. ............ 435/240
3711699 11/1988 European Pat. Off. ............ 435/240
8903872 5/1989 PCT Int'l Appl. ................ 435/240

OTHER PUBLICATIONS

Hirsch, J. D. and Margolis, F. L. (1979), Brain Res., 161:277–291.
Kleene, S. J. and Gesteland, R. C. (1981), Brain Res., 229–536–540.
Noble, et al., (1984) Neurosci. Letts., 45:193–198.
Gonzales, et al., (1985), J. Neurosci. Methods, 14:77–90.
Ronnett, Hester and Snyder: (1989), Neuroscience Abstracts, 12:749.
Coon, et al., (1989), Proc. Natl. Acad. Sci. USA, 86:1703–1707.
Calof, A. L. and Chikaraishi, D. M. (1989), Neuron, 3:115–127.
Pixley, S. K. and Pun, R. Y. K. (1990), Develop. Brain Res., 53:125–130.

*Primary Examiner*—David M. Naff
*Assistant Examiner*—Deborah K. Ware
*Attorney, Agent, or Firm*—Banner, Birch, McKie & Beckett

[57] ABSTRACT

Primary cultures of purified olfactory neurons can be stimulated with physiological levels of odorants. The neurons of the cultures express markers characteristic of mature olfactory neurons in vivo, such as vimentin, olfactory marker protein and neuron-specific enolase. The cultures are useful for screening for odorants and antagonists, as well as for biochemical and physiological studies of olfactory transduction.

5 Claims, 9 Drawing Sheets

PRIMARY CULTURE OF OLFACTORY NEURONS

This invention was made with government support under grants DA-00266 and NS-01231 awarded by The United States Public Health Service. The government has certain rights in the invention.

This application is a continuation of application Ser. No. 07/633,513, filed Dec. 31, 1990, now U.S. Pat. No. 5,217,893.

TECHNICAL FIELD OF THE INVENTION

This invention relates to the area of primary cell culture. More specifically it relates to culture of olfactory neuronal cells.

BACKGROUND OF THE INVENTION

Olfactory transduction discriminates with great accuracy and sensitivity among a multitude of volatile, low molecular weight compounds (Lancet, D. (1986) *Ann. Rev. Neurosci.*, 9:329-355; Snyder, S. H., Sklar, P. B. and Pevsner, J. (1988) *J. Biol. Chem.*, 263:13971-13974), but compared to visual transduction, it is relatively poorly understood. One difficulty lies in the heterogeneity of olfactory epithelium in which the olfactory neurons reside. The olfactory primary sensory neurons are located in a pseudostratified columnar epithelium consisting of three principal cell types (Graziadei, P. P. C. (1971) The olfactory mucosa of vertebrates. In: *Handbook of Sensory Physiology*, Vol. I. (Ed. Beidler, L. M.), Springer Verlag, Berlin, pp. 27-58). The sustentacular or supportive cells resemble glial cells and stretch from the epithelial surface of the basal lamina. Cell bodies of the sensory neurons lie at various levels in the epithelial layer and extend apical dendrites to the surface of the epithelium and unmyelinated axons through the basal lamina. The third cell type, the basal cell, underlies the receptor neurons and is thought to serve as a precursor population from which new olfactory neurons can arise. Isolation of receptor neurons from these other cell types has been difficult, thereby limiting ability to perform biochemical analysis.

Several attempts have been made to obtain populations of primary olfactory neurons. Initial efforts employed in vitro culture of the entire olfactory epithelium (Gonzales, et al., (1985) *J. Neurosci. Methods*, 14:77-90; Noble et al., (1984) *Neurosci. Letts*, 45:193-198). N-ethylmaleimide has been used to dissociate olfactory epithelium cells into single cells, which, however, lose excitable properties (Kleene, S. J. and (Gesteland, R. C. (1981) *Brain Res.*, 229:536-540). Hirsch, J. D. and Margolis, F. L. (1979) *Brain Res.*, 16:277-291, have employed enzymatic dissociation followed by general mechanical disruption with dissociated cells centrifuged through a bovine serum albumin (BSA) gradient, yielding a partially purified population of cells. Others (Calof, A. L. and Chikaraishi, D. M., (1989) *Neuron*, 3:115-127; Pixley, S. K. and Pun, R. Y. K. (1990) *Develop. Brain Res.*, 53:125-130) have devised methods to perform lineage analysis and electrophysiologic studies on embryonic olfactory neuronal cells but the neuronal cells were not in pure cultures and were, therefore not amenable to biochemical studies.

Thus there is a need in the art for relatively pure populations of primary olfactory neurons which retain their excitability in response to odorants.

BACKGROUND OF THE INVENTION

It is an object of the invention to provide a primary culture of olfactory neurons, substantially purified from other olfactory epithelial cells.

It is another object of the invention to provide a primary culture of olfactory neurons which is responsive to odorants.

It is yet another object of the invention to provide a method of producing primary cultures of olfactory neurons.

It is still another object of the invention to provide a test kit for determining the effects of odorants on olfactory neurons.

It is an object of the invention to provide a method of identifying odorants.

It is still another object of the invention to provide a method for identifying antagonists of known odorants.

These and other objects of the invention are provided by one or more of the embodiments which are described below. In one embodiment of the invention a primary culture of olfactory neurons is provided which is substantially purified from sustentacular cells and basal cells. The cultured neurons demonstrate responsiveness to physiologic levels of odorants. The cultured neurons express vimentin, olfactory marker protein and neuron-specific enolase. The cultured neurons do not express glial fibrillary acidic protein, S-100 protein, keratin, or neurofilament protein.

In another embodiment of the invention a method of producing primary cultures of olfactory neurons is provided. The method comprises the steps of:

providing olfactory epithelium of an animal;

disrupting the olfactory epithelium to separate cells of said olfactory epithelium;

passing the separated cells of said olfactory epithelium through a mesh having a pore size of between about 10 and 25 microns to remove cell aggregates;

plating said separated cells in a nutrient medium comprising D-valine, cytosine arabinoside, and nerve growth factor (NGF), on a solid substrate.

In still another embodiment of the invention a test kit is provided for determining the effects of odorants on olfactory neurons. The test kit comprises: a primary culture of olfactory neurons, substantially purified from sustentacular cells and basal cells on a solid support, said neurons demonstrating responsiveness to physiologic levels of odorants, said neurons expressing vimentin, olfactory marker protein and neuron-specific enolase, said neurons not expressing glial fibrillary acidic protein, S-100 protein, keratin, or neurofilament protein; and a means for testing neuronal excitation.

In yet another embodiment of the present invention a method for identifying antagonists of known odorants is provided. The method comprises the steps of:

exposing the primary culture of olfactory neurons of the present invention to a known odorant and determining a first level of excitation of the neurons;

exposing the primary culture of olfactory neurons to a mixture of the known odorant and a putative antagonist and determining a second level of excitation of the neurons;

comparing said first and second excitation levels, an antagonist being identified when the second level of excitation is less than the first level of excitation.

In still another embodiment of the invention a method for identifying new odorants is provided. The method comprises the steps of:

exposing the primary culture of olfactory neurons of the present invention to a putative odorant and determining a level of excitation of the neurons, an odorant being identified which increases the level of excitation of the culture over a basal level, said basal level determined in the absence of the putative odorant.

These and other embodiments of the invention which will be described in more detail below, provide the art with a potent tool to investigate olfactory transduction.

BRIEF DESCRIPTION OF THE DRAWINGS

FIG. 1 shows phase-contrast microscopy of cultures of olfactory neurons. FIG. 1A is within 2 hours of plating; FIG. 1B is 24 hours after plating; FIG. 1C is 72 hours after plating.

FIG. 2 shows immunocytochemistry of neonatal rat nasopharyngeal sections.

FIG. 3 shows immunocytochemical staining of primary cultures of rat olfactory neurons. Phase-contrast (FIGS. 3A, 3C, 3E, 3G, 3I, and 3K) and immunofluorescent (FIGS. 3B, 3D, 3F, 3H, 3J, and 3L) images are shown. FIGS. 3A and 3B, olfactory neuronal culture stained positively for OMP. FIGS. 3C and 3D, anti-vimentin antibodies stain olfactory neurons diffusely, highlighting neurites. FIGS. 3E and 3F, there is no detectable staining with anti-S-100 antibodies. FIGS. 3G and 3H neuron specific enolase antibodies stain olfactory cell bodies. FIGS. 3I and 3J, occasionally, a GFAP positive cell can be visualized which has extremely different morphology. FIGS. 3K and 3L, non-immune serum reveals no detactable staining.

FIG. 5 demonstrates immunocytochemical staining of cells trapped by filtration during preparation of primary cultures. Primary cultures were prepared. Cellular material trapped during filtration was resuspended in medium and plated. Phase-contrast (FIGS. 5A, 5C, 5E, 5G, and 5I) and immunofluorescent image (FIGS. 5B, 5D, 5F, 5H, 5J) pictures are shown. FIGS. 5C and 5D, epithelial clusters do not demonstrate positive staining for OMP. FIGS. 5E and 5F, anti-keratin antibody recognizes small clusters of cells, which may represent aggregates of basal cells. FIGS. 5G and 5H, at higher magnification, the large cluster of putative epithelial cells does not stain for keratin, while the small cluster seen is quite positive. FIGS. 5I and 5J, non-immune serum demonstrates no staining in these cultures.

FIG. 6 demonstrates an evaluation of various matrix substrate substances for morphology and plating efficiency of olfactory neurons. Cell cultures were prepared and plated on substrates. Phase-contrast (FIGS. 6A, 6C, 6E, 6G, 6I, 6K, 6M, 6O, 6Q, and 6S) and phase-contrast immunofluorescent (FIGS. 6B, 6D, 6F, 6H, 6L, 6N, 6P, 6R, and 6T) images are shown.

FIG. 7 shows the effect plating of primary cultures onto matrigel compared to laminin.

FIG. 8 demonstrates the effect of NGF on olfactory neuron survival. Olfactory neurons were grown either with (FIG. 8A) or without (FIG. 8B) NGF at a concentration of 25 ng/ml.

DETAILED DESCRIPTION OF THE INVENTION

It is the discovery of the present invention that primary cultures of olfactory neuronal cells can be obtained which retain their responsiveness to odorants in vitro. These cultures are substantial purified from other cell types, including other olfactory epithelial cells, fibroblasts and mesenchymal cells. The high level of purity of the cells which has been obtained renders the cultures highly suitable for biochemical studies of olfactory transduction. The polyclonality of the cell cultures suggests that they encompass the entire spectrum of odorant responsiveness.

The cultures of the present invention contain predominantly olfactory neurons. Typically they contain greater than about 85% neurons. Often they contain greater than about 90% neurons. Preferably they contain greater than about 95% or 98% neurons. The level of purity can be assessed by a number of criteria. Certain proteins are characteristic of olfactory neuronal cells and their presence can be determined and quantitated. These include olfactory marker protein (OMP), neuron-specific enolase (NSE), and vimentin. Other proteins are characteristically absent from olfactory neuronal cells and their presence can also be determined and quantitated. These include S-100 protein, glial fibrillary acidic protein, neurofilament protein, and keratin. As is known in the art there are many ways to determine the presence of particular proteins in cell populations. Any of these may be used in the assessment of purity of the cell cultures. Particularly suitable methods are immunological, and include immunohistochemistry and Western blotting.

The cells of the olfactory epithelium from which the neuronal cells have been purified are mainly the sustentacular cells and the basal cells. These cells can be distinguished on the basis of morphology, marker proteins, and lack of excitability. The cultured neuronal cells of the present invention are responsive to physiologic levels of odorants, which may vary from odorant to odorant. However, generally these are exceedingly low levels, in the range of 1 nM to 10 uM. For example, the neuronal cultures of the present invention are stimulated to 50% of their maximal adenylyl cyclase augmentation at 1 nM by 2-isobutyl-3-methoxypyrazine (IBMP), whereas comparable levels of excitation are elicited by between about 1–10 uM of citralva or isovaleric acid.

Primary cultures comprise cells which are taken directly from a whole animal source. They are not continuous cultures, and have a limited time-span of survival in culture. Typically the life-span in culture is in the range of 1 to 2 weeks. The neuronal cells of the present invention are typically mature cells and do not divide.

The neuronal cell cultures of the present invention may be derived from any of a variety of animal sources. For example, chickens, rats, and frogs have been used to study olfaction previously and are suitable for use in the present invention. Preferred animal sources are mammals. Although the applicants do not wish to be bound by any particular theory, neonatal tissue may be advantageous as a source material for the neuronal cell cultures.

According to the method of the present invention, the olfactory epithelium cells are obtained by dissection as is known in the art. A suspension of olfactory epithelium cells is prepared by means of mechanical and enzymatic disruption of the tissue structure. The tissue can first be minced to provide small pieces of tissue, e.g., of approximately 1 mm$^2$. A combination of enzymes may be used to separate the cells from each other, including hyaluronidase, DNAse, collagenase, and dispase. Typically these enzymes are incubated with the tissue at 37° C. to digest the substances which may bind and aggregate the cells to each other. The tissue can also be mechanically disrupted by any means known in the art, such as trituration, Waring blender, Potter-Elvehjem homogenizer, meat grinders, shakers, etc.

According to the method of the present invention, neuronal cells are purified from other olfactory epithelium cells by means of a size fractionation procedure. The size fractionation can be conveniently accomplished by passing a suspension of epithelial cells through a mesh of defined pore size or spacing intervals. The meshes may be made of any materials although wire and nylon meshes may be convenient and readily available. The meshes may range in size from about 150 microns to 10 microns, preferably from about 25 to 10 microns. Preferably the epithelial cell suspensions are passed through meshes of increasingly smaller sizes. The size fractionation purifies neuronal cells because the other cells of the olfactory epithelium aggregate in larger clumps than the mesh and thus can be filtered out from the cell suspensions. The neuronal cells appear to dissociate into single cell units and not to re-aggregate, therefore permitting passage through the pores of the meshes.

The size fractionated cells can be resuspended in a nutrient medium. Many nutrient media are known in the art for animal cells and may be used in the practice of the present invention. However, it has been found to be particularly advantageous to include D-valine, and cytosine arabinoside in the medium as selective agents. D-valine is selective for epithelial cells, and inhibits growth of fibroblasts and mesenchyme cells which may contaminate the neuronal cell suspension. Cytosine arabinoside inhibits the growth of dividing cells, thereby selecting mature, non-dividing cells, such as the neuronal cells. It is a finding of the present invention that NGF (nerve growth factor) which is necessary for growth for some types of neurons but not others, is necessary for survival of olfactory neurons.

The cell suspensions of the present invention can be plated on a solid support such as a glass slide or plastic tissue culture dish. It is preferred that a matrix substance such as laminin be adhered to the solid support to provide a solid substrate for attachment of the cells. Laminin provides an additional degree of selectivity to the method of culturing neuronal cells, because neuronal cells attach to it, but fibroblasts do not. Other matrix substances such as fibronectin or Matrigel ™ (reconstituted basement membrane, available from Collaborative Research) can also be used, although laminin appears to provide superior results.

The present invention also contemplates test kits for determining the effects of odorants on olfactory neurons. The kits comprise the primary cultures of olfactory neurons of the present invention on a solid support. In addition, a means for testing neuronal excitation is included. The means for testing neuronal excitation can be the substrates for measuring cyclic AMP, which is produced upon excitation of neurons. Typically the means for testing cyclic AMP levels will be the components of a radioimmunoassay, such as is commercially available from NEN/DuPont, Boston, MA. Other means for testing for neuronal excitation can also be employed, such as patch clamp recording techniques.

The neuronal cell cultures of the present invention can be used to screen compounds for their effects on olfactory tissues. For example compounds can be screened for their ability to stimulate the neuronal cells above their basal level of excitation. Such compounds are known as odorants. Stimulation can be measured by any means known in the art to correlate with excitation of the neuronal cells. These means include electrophysiological measurements such as patch clamp recording, as well as biochemical means such as measuring the accumulation of cyclic AMP or the increase in specific activity of adenylyl cyclase.

Alternatively, compounds can be screened for their ability to block the excitation of neuronal cells by known odorants. Such compounds are called antagonists. Antagonism can readily be determined by exposing the cultures of the present invention to the odorant alone, and to the odorant in admixture with a putative antagonist. A decrease in the level of excitation in the presence of the putative antagonist relative to the control levels in the presence of odorant only, identifies an antagonist.

EXAMPLE 1

This example describes the isolation of purified olfactory neuronal cell cultures.

Olfactory tissue from neonatal rats was collected, minced, dissociated in enzymes and plated on chamber slides pretreated with laminin as described below.

Approximately 3 litters or 28–32 pups were used per prep. The 2–3 day old rat pups were sacrificed by decapitation, and olfactory tissue dissected and immediately placed in modified Eagle's medium (MEM) containing 4.8 g/l of HEPES buffer, designated MEM-AIR. The turbinates were transferred twice through fresh MEM-AIR to minimize contamination. Tissue was then centrifuged at 700×g for 7 min. After the supernatant was decanted, the tissue was minced to achieve tissue fragments of approximately 1 mm in size, resuspended in MEM-AIR and centrifuged at 700×g for 7 min. Tissue was then placed in 30 ml of MEM-AIR containing 196 (w/v) BSA, RIA grade (Sigma), 50 ug/ml DNAse (Sigma, St. Louis, Mo.), 1/ mg/ml hyaluronidase (Sigma, 1 mg/ml collagenase (Worthington Biochemical, Freehold, NJ), and S mg/ml dispase (Boehringer-Mannheim Biochemicals, Indianapolis, Ind., and incubated with agitation for 1 hr at 37° C. At the end of incubation, the cell suspension was triturated 10 times with a 10 ml plastic pipet and passed through a 150 micron wire mesh. The cell suspension was then centrifuged at 500 x g for 5 min. The supernatant was aspirated and the cell pellet resuspended in plating medium composed of modified Eagle's medium containing D-valine (MDV, Gibco, Grand Island, NY) containing 15% (v/v) dialyzed fetal calf serum (dFCS, (Gibco), 5% (v/v) NU serum (Collaborative Research, Bedford, MA), 10 uM cytosine arabinoside (ara C) and 25 ng/ml nerve growth factor (NGF, Collaborative Research). After resuspension, cells were successively filtered through 50 micron and 10 micron nylon mesh filters (Small Parts, Miami, Fla,), to remove any remaining undigested clumps of cells and epithelial cells. Cells were plated at a density of 1 x 106 cells per cm$^2$ into tissue culture dish (Falcon, Lincoln Park, NJ) or Labtek tissue culture slides (Nune, Naperville, Ill.) coated with MDV containing laminin at 25 ug/ml (Collaborative Research). Cultures were placed in a humidified 37° C. incubator receiving 5% CO2. On day 2 and every day thereafter, cells were fed with MDV containing 15% dFCS, gentamicin, kanamycin, NGF and ara C.

Figure 1D:
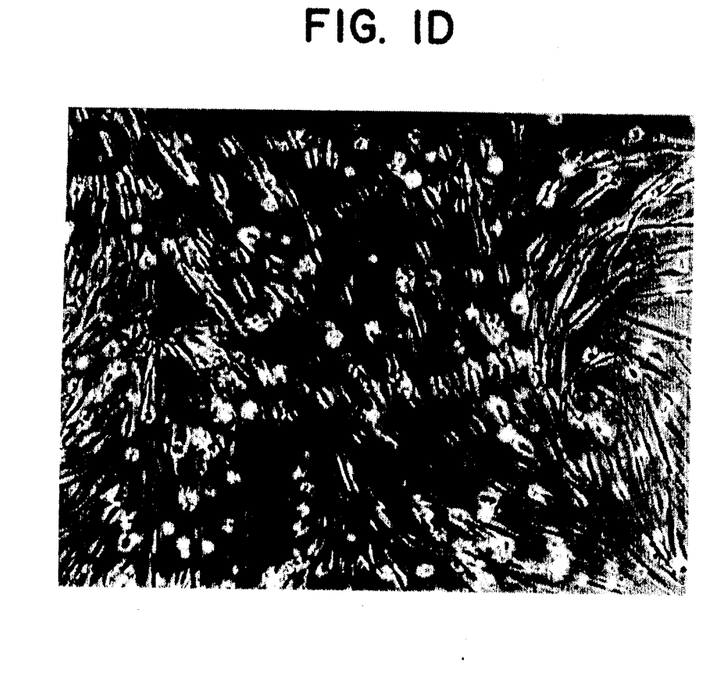
FIG. 1D shows a low-magnification image at 72 hours.
Figure 1E:
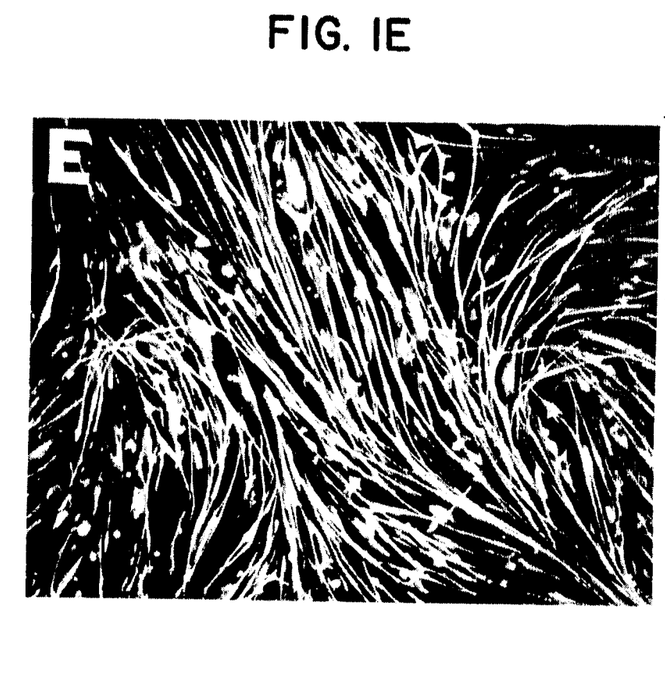
FIG. 1E shows neuronal processes stained with anti-vimentin antibodies and fluorescenated secondary antibody.

Within 2 hr after plating, cells attach and began to spread (FIG. 1A). After 24 hr in culture, cells began to distribute more uniformly on the culture surface and extended a short multi-branched process and an opposing long unbranched process (FIG. 1B). At 72 hr in culture, cells reached a uniform distribution (FIG. 1C), and most non-neuronal cells died off. Neurite outgrowth appears random (FIG. 1D); cell processes are extremely long, about 20–50 cell body lengths and can be better visualized by immunofluorescence, using anti-vimentin antibodies (FIG. 1E).

EXAMPLE 2

This example describes lmmunocytochemical and lmmunoblotting characterization of the primary cultures of the invention.

Immunohistochemistry was performed on neonatal rats the same age as those utilized tn primary culture preparation. Animals were perfused with. PBS and then 4% paraformaldehyde in PBS. Olfactory tissue was dissected and post-fixed in 4% PFA for 2 hr at room temperature. Thereafter, tissue was sunk in PBS containing 15% (w/v) sucrose, embedded in brain paste and sectioned on a cryostat.

For immunocytochemistry, cells were plated in two-chamber Labtek tissue culture slides previously treated with MDV containing 25 ug/ml laminin. After 5–7 days in culture, the upper chamber of the slides was removed and slides were rinsed quickly three times at 37° C. in phosphate-buffered saline (PBS), pH 7.3. Slides were immediately placed in PBS containing 4% (w/v) paraformaldehyde at 37° C. and incubated for 20 min. Alternatively for immunofluorescence, primary culture cells plated on slides were quickly rinsed 3 times with PBS at 37° C., and placed in methanol at −20 C. for 15 min. Monolayers treated in either manner were then washed 3 times for 5 rain each in PBS at room temperature, permeabilized by incubation in 0.1% (w/v) Triton-X-100 (T-X-100) for 15 rain, and rinsed again 3 times in PBS. When chromagen was used, endogenous peroxidase activity was quenched by incubation of slides in PBS containing 2% (v/v) hydrogen peroxide, followed by 3 rinses in PBS. Nonspecific staining was blocked by incubation for 1 hr with non-immune serum, appropriate for the secondary antibody, at a dilution of 1:100 in PBS containing 1% (w/v) BSA. Slides were then incubated in PBS containing 1% BSA and primary antiserum overnight at 4° C. The next day, the slides were rinsed three times with PBS, blocked with PBS containing 1% BSA and incubated for 2 hr at 25° C. with the appropriate biotinylated secondary antibody using Vectastain kits (Vector Labs, Burlingame, CA). Slides were again washed in PBS, blocked, incubated for 1 hr in PBS containing 1% BSA in the avidin-biottin-horseradish peroxidase complex (Vector Labs), rinsed, and incubated for 5 rain with the chromogen, 3-amino-9-ethylcarbazole (AEC, Biomeda Corporation, Foster City, CA). For immunofluorescence, primary antiserum at the appropriate dilution was added to slides in PBS containing 1% BSA and incubated overnight at 4° C. The next day, slides were washed three times for 5 rain each in PBS and incubated in PBS containing 1% BSA and the appropriate fluorescenated or rhodaminated antibody (Jackson Immunoresearch Laboratories Incorporated, West Grove, PA). Slides were subsequently washed three times in PBS, and phase and fluorescent pictures were immediately taken.

Antisera were used at the following dilutions: monclonal anti-vimentin antibody (Boehringer-Mannheim) at 1:3 dilution; polyclonal anti-neuron specific enolase (NSE) antibody (IncStar, Stillwater, MN) at 1:4 dilution; polyclonal anti-S-100 antibody (IncStar) at 1:4 dilution; polyclonal anti-tubulin antibody (Dr. Douglas Murphy, Johns Hopkins University School of Medicine, Baltimore, MD) at 1:250 dilution; polyclonal anti-olfactory marker protein (OMP) antibody (gift of Dr. Frank Margolis, Roche Institute, Nutley, NJ) at 1:300 dilution; anti-glial fibrillary acidic protein (GFAP, DAKO-Patts, Santa Barbara, CA) at 1:800 dilution; and non-immune serum as control (Vector Labs) at 1:100 dilution.

Figure 2A:
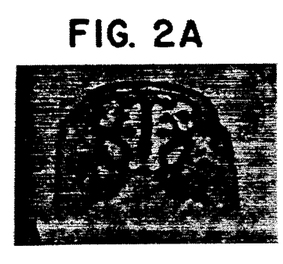
FIG. 2A, low-power of coronal section stained for OMP.
Figure 2B:
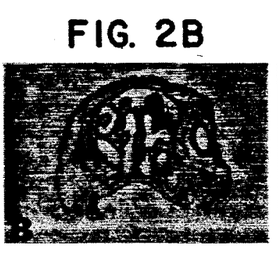
FIG. 2B, a more caudal section demonstrates OMP-positivity in the epithelium and on fibers converging on the bulb.
Figure 2C:
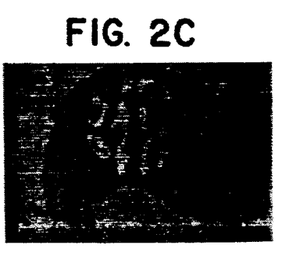
FIG. 2C, low-power coronal sections stained for vimentin.
Figure 2D:
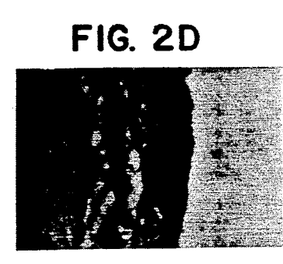
FIG. 2D, staining of olfactory epithelium for OMP.
Figure 2E:
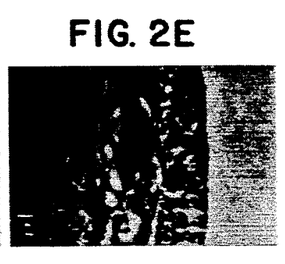
FIG. 2E, staining for vimentin.
Figure 2F:
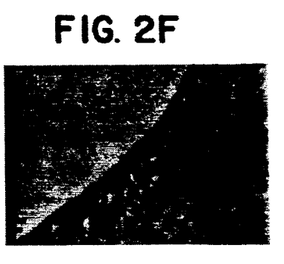
FIG. 2F, staining of olfactory epithelium for neuron specific enolase.
Figure 2G:
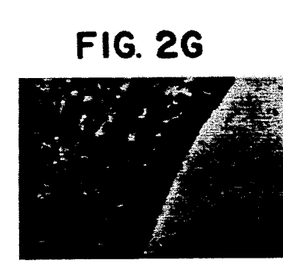
FIG. 2G, staining of olfactory tissue for tubulin.
Figure 2H:
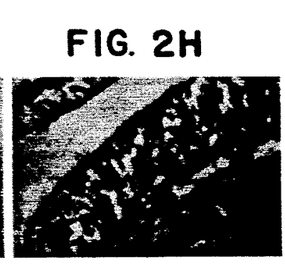
FIG. 2H, staining of olfactory epithelium with anti-keratin antibodies.
Figure 2I:
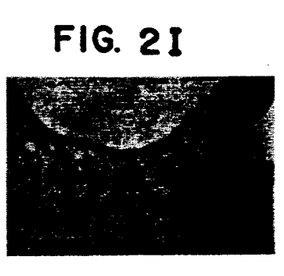
FIG. 2I, staining of olfactory epithelium for GFAP.
Figure 2J:
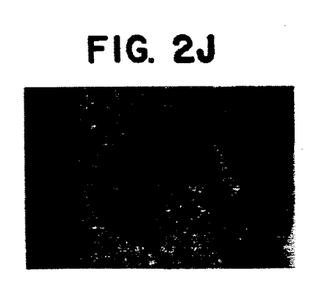
FIG. 2J, staining with non-immune control serum.

At low magnification (FIGS. 2A–C), the olfactory epithelium appears as frond-like projections extending towards the midline septum. The olfactory epithelium and the primary axons, which extend towards the bulb, stain positively for OMP (FIGS. 2A, B). Unlike other neuronal cells, the axons of olfactory neurons contain the intermediate filament vimentin (Schwob et al., 1986 J. Neurosci. 6:208–217), whose immunoreactivity is apparent in olfactory primary axons as they converge upon the olfactory bulbs (FIG. 2C). At higher magnification, while OMP is evident in the epithelium containing neuronal cell bodies and the submucosal axonal process (FIG. 2D), vimentin is localized in the submucosal region containing the primary axons (FIG. 2E). Neuron specific enolase (NSE) immunoreactivity is also localized selectively to olfactory mucosa (FIG. 2F). Tuburin occurs diffusely throughout the mucosa, but with greater density at the luminal surface, which contains cilia (FIG. 2G). Anti-keratin antibodies stain the basal cell layer (FIG. 2H). Anti-(GFAP antibodies stain the submucosal region (FIG. 2I), presumably reflecting glial-like cells which surround olfactory axons. Staining of olfactory tissue with non-immune serum is shown in FIG. 2J.

Figure 3A:
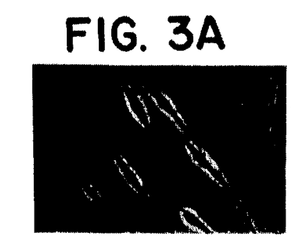
Figure 3B:
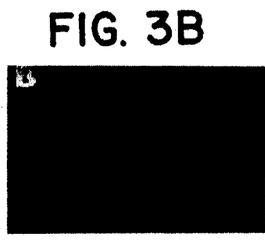
Figure 3C:
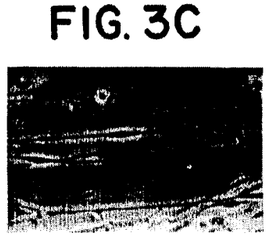
Figure 3D:
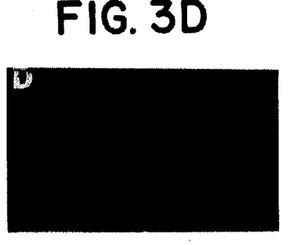
Figure 3E:
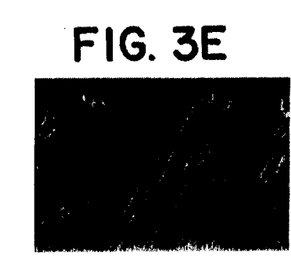
Figure 3F:
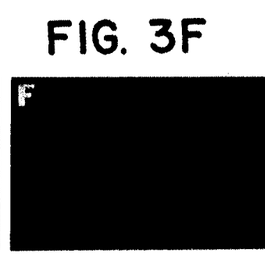
Figure 3G:
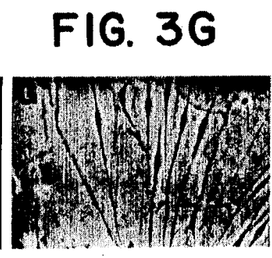
Figure 3H:
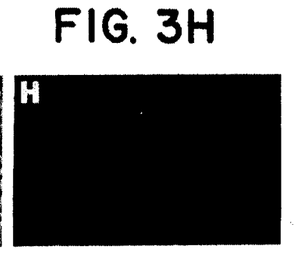
Figure 3I:
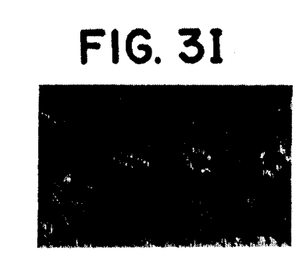
Figure 3J:
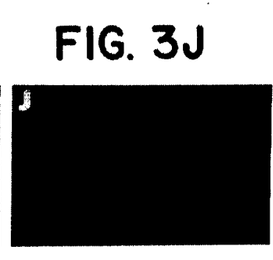
Figure 3K:
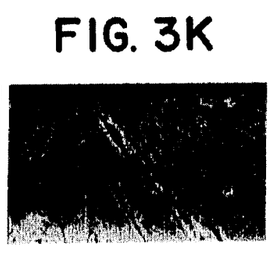
Figure 3L:
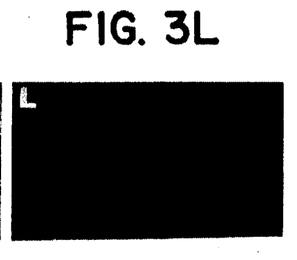

Like olfactory neurons in intact tissue, olfactory neurons in primary culture stain positively using anti-OMP antibodies (FIGS. 3A, 3B), anti-vimentin antibodies (FIGS. 3C, D), and anti-NSE antibodies (FIGS. 3G. H). No staining of primary cultures is seen using anti-S-100 antibody (FIGS. 3E, F). Occasional GFAP-positive cells are seen (FIGS. 31, J), which have distinctive morphology; none or the bipolar cells stain positively for GFAP. No staining is seen when non-immune serium is usa in place of primary antiserum (FIGS. 3K, L). Thus, cultures of rat primary olfactory neurons stain specifically for those markers found in neurons in vivo. Immunofluorescence was used for primary cultures as positive staining in the processes is not adequately demonstrated by peroxidase.

Figure 4:
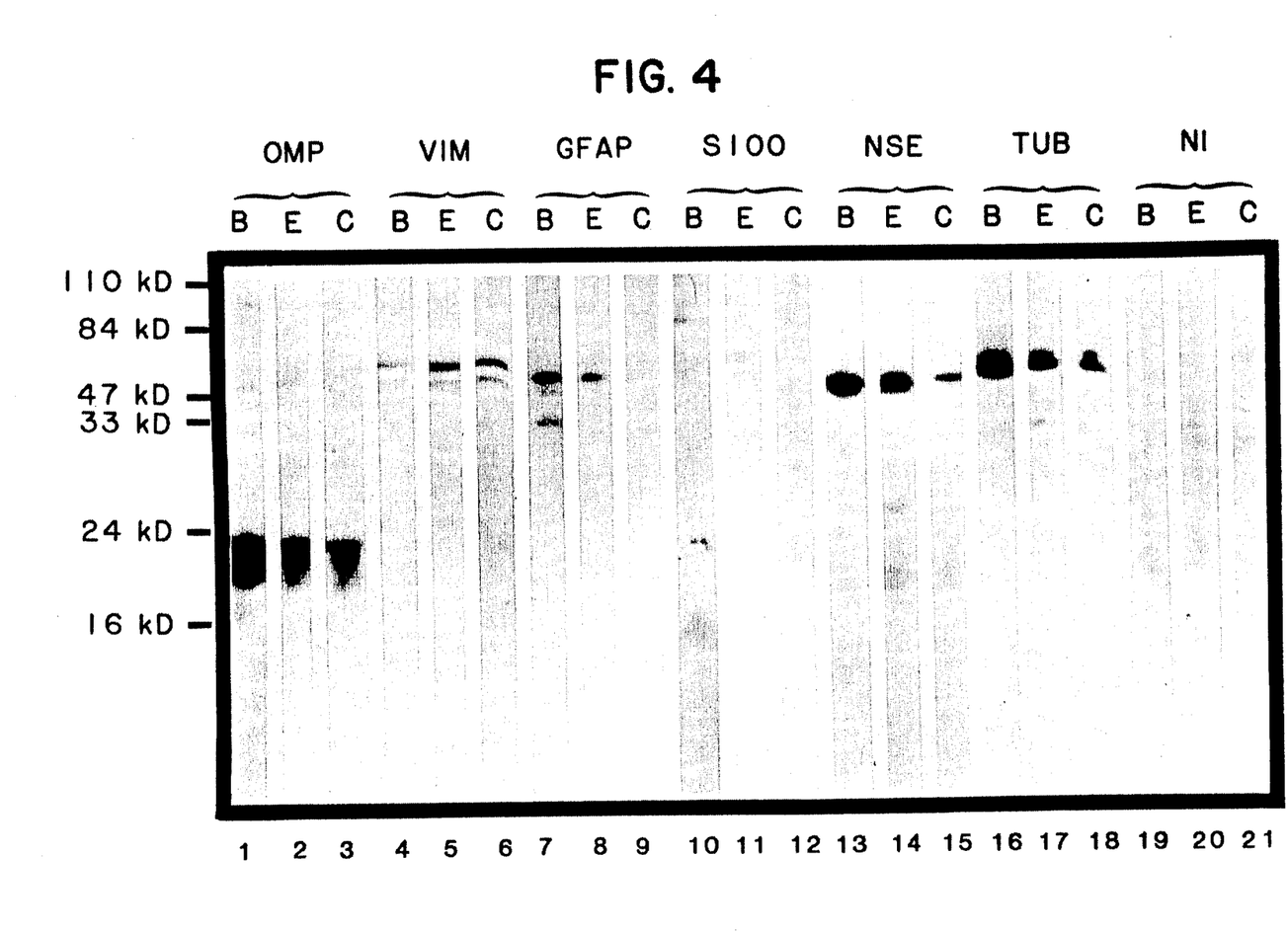
FIG. 4 shows a Western blot analysis of extracts of olfactory neurons in culture. Tissue from olfactory bulb (b), olfactory epithelium (E), or primary cultures of olfactory neurons (C) were prepared. Extracts were run on PAGE and Western blot analysis performed. All three extracts show detectable OMP (lanes 1-3) Likewise, vimentin is present in all three tissues (lanes 4-6). GFAP is detectable in olfactory bulb and epithelium, but not in cultures (lanes 7-9). S-100 is detectable in bulb, but not in epithelium or cultured material (lanes 10-12). Both NSE (lanes 13-15) and tubulin (lanes 16-18) are detectable in all three tissues. No staining is seen when non-immune serum is utilized (lanes 19-21).

To conform the specificity of staining in both tissue sections and in primary cultures of olfactory neurons, Western blot analysis was performed (FIG. 4).

Sodium dodecyl sulfate polyacrylamide gel electrophoresis (SDS-PAGE) was performed according to the method of Laemmli (1971), utilizing a 14-20% gradient. Western blotting employed the method of Speicher (1980) *Proc. Natl. Acad. Sci. USA*, 77:5673-77, with several modifications. Gels were transferred to nitrocellulose paper at 60 V for 5 hrs at 4° C. At the end of this time, gels were rinsed in water and blocked in buffer containing 0.15 M NaCl, 0.05 M Tris-HC1, 0.05% sodium azide, and 2% (w/v) RIA-grade BSA for 12 hr at 4° C. The next day, blots were washed 3 times in PBS. For rabbit antisera, the primary antiserum was placed in blocking buffer containing antiserum at the appropriate dilution, 2% BSA and 0.05% tween-20. Incubation was performed overnight at 4° C. The next day, blots were washed three times in PBS containing 0-0.05% tween. Blots were incubated in $^{125}$I-protein A in blocking buffer containing 2% BSA and 0.05% tween for 1 hr at room temperature. Thereafter, blots were washed 3 times in PBS with 0.05% tween, and exposed to X-omar (Kodak, Rochester, NY) film. For monoclonal mouse antibodies, blots were washed in PBS without tween and incubated in primary antibody at the appropriate dilution in blocking buffer containing 2% BSA and 3% normal serum overnight at 4° C. The next day, blots were rinsed 5 times with PBS, and incubated in blocking buffer containing 2% BSA and rabbit anti-mouse IgG at 1:100 dilution (Jackson Labs) for 1 hr at room temperature. Blots were again rinsed 3 times in PBS and mouse peroxidase anti-antiperoxidase complex (Sternberger-Meyer, Jarrettsville, MD) at 1:200 dilution in blocking buffer with 2% BSA for 1 hr at room temperature. Blots were again rinsed 3 times in PBS, once in 50ram Tris, pH 7.6 and then incubated in AEC for 30 sec.

Tissue was collected from olfactory bulb (B), olfactory epithelium (E) and primary olfactory cultures (C). Extract (100 ug per lane) was loaded on a 14-20% SDS-PAGE gel, electrophoresed, and transferred to nitrocellulose paper. Blots were incubated with antibodies against OMP (FIG. 4, lanes 1-3), anti-vimentin antibodies (FIG. 4, lanes 4-6), anti-GFAP antibodies (FIG. 4, lanes 7-9), anti-S-100 antibodies (FIG. 4, lanes 10-12) anti-NSE antibodies (FIG. 4, lanes 13-15), anti-tubulin antibodies (FIG. 4, lanes 16-18) and non-immune serum in place of primary antiserum (FIG. 4, lanes 19-21). Antibodies against OMP recognize a band of appropriate molecular weight in all three tissues. Anti-vimentin antibodies recognize a band of appropriate molecular weight in bulb an olfactory epithelium extract, as would be expected given the mesenchymal elements present in these tissues, as well as in the primary olfactory cells whose axons contain vimentin. Although antibodies against GFAP detect a band of appropriate mobility in olfactory bulb and olfactory epithelium, no such band is seen upon incubation with olfactory cultured extracts. While immunofluorescence (FIG. 3 I and J) demonstrates the presence of occasional GFAP-positive cells, levels of GFAP are presumably too low to be detected by Western blotting. Antibodies against S-100 protein recognize a band of appropriate molecular weight in olfactory bulb, but not in olfactory epithelium or primary cultures. NSE immunoreactivity of appropriate molecular weight is evident in bulb, olfactory epithelium and primary cultures. Antibodies against tubulin detect a doublet of appropriate molecular weight in all three tissues, while non-immune serum fails to identify the major band sin any of the three extracted tissues. Thus, Western blot analysis confirms the specificity of staining seen by immunocytoehemistry of primary cultures of rat olfactory neurons.

EXAMPLE 3

This example describes the immunocytochemieal characterization of cells removed from the primary cell cultures by filtration according to the method of the invention.

A procedure to prepare olfactory neurons from dissociated cells of olfactory mucosa includes entrapment of epithelial cells on a 50 micron filter just prior to plating. Perhaps due to differences in extracellular matrix components, the epithelial cells, which probably include epithelial and sustentacular cells, remain associated or reassociate so that they are trapped by filtration. Some neurons are trapped as well. Epithelial cells generally appear flat and polygonal, but after 5-7 days in cultures they may appear fusiform, although they do not extend processes similar in length or diameter to the primary neurons seen in the flow-through. The epithelial cells trapped on the filters were characterized immunocytochemically (FIG. 5). Cellular material trapped on filters was eluted into plating medium and plated in a similar manner to olfactory neurons. Fixation and immunocytochemical staining was performed as described above.

Figure 5A:
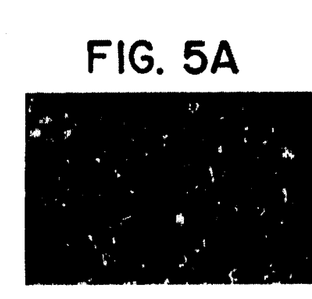
FIGS. 5A and 5B, epithelial cell clusters do not stain positively for vimentin; however, occasionally a trapped putative olfactory neuronal cell is seen, which does stain positively for vimentin.
Figure 5B:
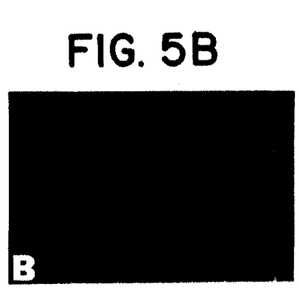
Figure 5C:
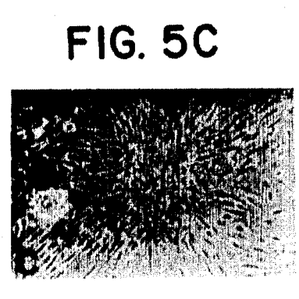
Figure 5D:
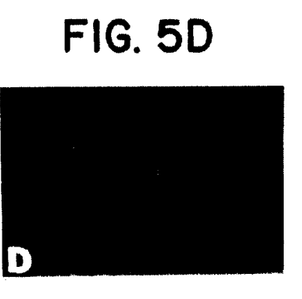
Figure 5E:
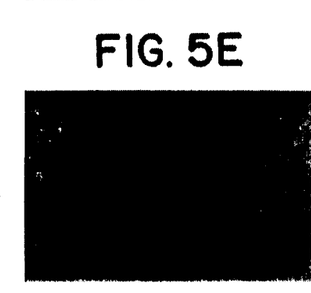
Figure 5F:
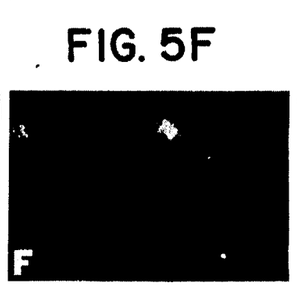
Figure 5G:
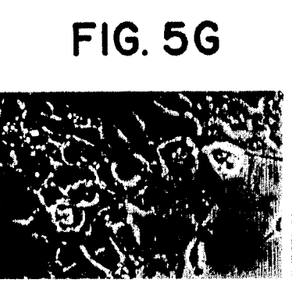
Figure 5H:
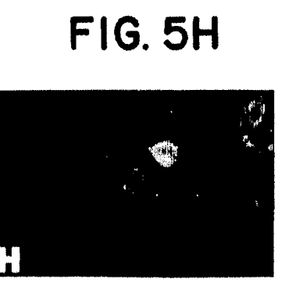
Figure 5I:
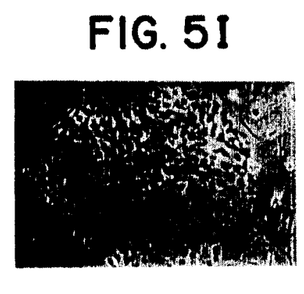
Figure 5J:
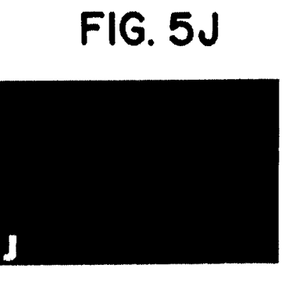
Figure 6A:
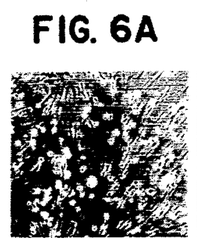
FIGS. 6A and 6B, laminin.
Figure 6B:
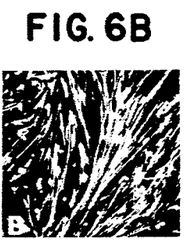
Figure 6C:
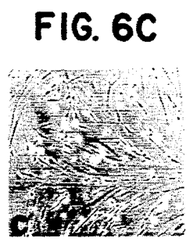
FIGS. 6C and 6D fibronectin.
Figure 6D:
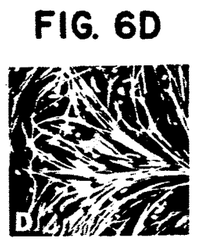
Figure 6E:
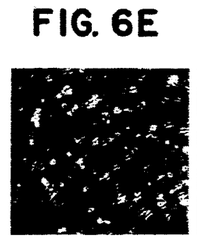
FIGS. 6E and 6F, fibronectin and laminin.
Figure 6F:
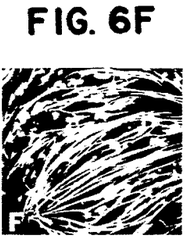
Figure 6G:
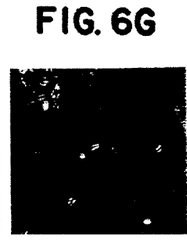
(FIGS. 6G and 6H poly-D-lysine.
Figure 6H:
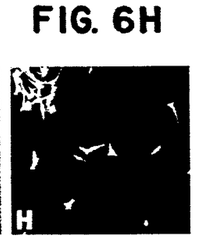
Figure 6I:
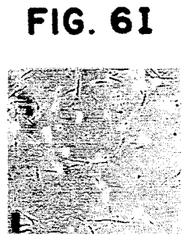
FIGS. 6I and 6J, polyornithine (PORN)
Figure 6J:
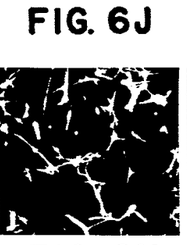
Figure 6K:
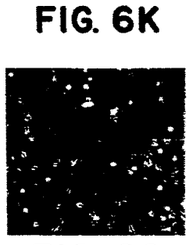
FIGS. 6K and 6L laminin and PORN.
Figure 6L:
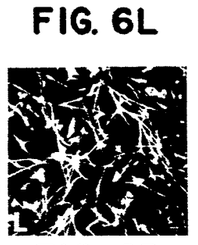
Figure 6M:
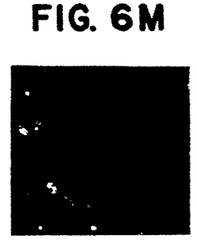
FIGS. 6M and 6N, heparan sulfate.
Figure 6N:
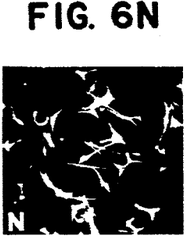
Figure 6O:
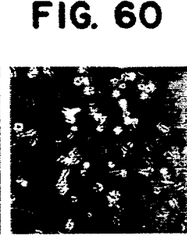
FIGS. 6O and 6P collagen.
Figure 6P:
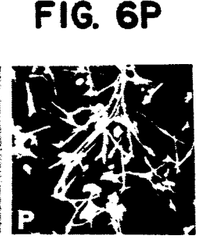
Figure 6Q:
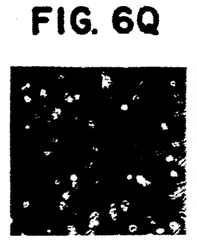
FIGS. 6Q and 6R, collagen IV.
Figure 6R:
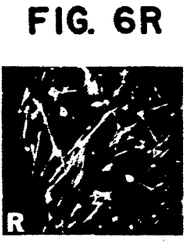
Figure 6S:
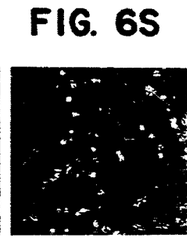
FIGS. 6S and 6T laminin treatment.
Figure 6T:
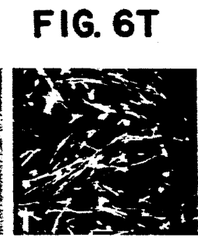

In contrast to olfactory neurons, epithelial cells do not stain for vimentin (FIGS. 5A and B). An occasional putative neuronal cell is retained along with the epithelial cells and does stain for vimentin (FIGS. 5A and B). Epithelial cells do not stain for OMP (FIGS. 5C and D). Basal cells are apparently trapped on filters as well, as small clumps of cells stain positively for keratin found In basal cells in vivo FIGS. 5E-H). No staining is seen using non-immune serum (FIGS. I and J). Thus, a substantial part of cellular selection is achieved by filtration, which apparently traps the majority of epithelial cells. Although after a week in culture these cells acquire spindle-shaped morphology, they are initially rounded and polygonal and therefore can easily be differentiated from neurons. In addition, their staining patterns differ from neuronal cells.

EXAMPLE 4

This example describes the effects of various substrate matrix substances on culture characteristics of olfactory epithelium cells.

To determine the role of substrate matrix substances on plating efficiency and on cellular selection, a number of different substrates were tested.

Two chamber slides were pretreated in a number of ways. For laminin coating, 1 ml of MDV containing 25 ug/ml laminin was plated onto glass two-chamber slides overnight at 37° C.; before use, the slides were rinsed with MDV. For fibronectin, slides were treated with a solution containing 1 ml of MDV containing 20 ug/ml fibronectin (Collaborative Research), incubated overnight at 37° C., and rinsed with MDV prior to use. For polyornithine (PORN, Sigma Chemicals), a solution at a concentration of 1 mg/ml PORN in deionized distilled water was added to slides, incubated 1 hr at rinsed twice with deionized distilled water, anti rinsed once with MDV prior to use. When laminin was used on PORN-treated slides, slides were treated with PORN and then laminin in the usual manner. Coating of slides with poly-D-lysine was performed analogous to treatment with polyornithine. Heparan sulfate was diluted in MDV to a concentration of 10 ug/ml and 1 ml was placed on a slide, maintained overnight at 37° C., and rinsed with deionized distilled water prior to use. Collagen (Gibco) or collagen IV (Collaborative Research) was prepared as a 50 ug/ml solution in deionized distilled water and 1 ml of this solution utilized per slide. In the ease collagen, the solution was allowed to air dry. Collagen IV was maintained overnight at room temperature, aspirated, air dried and then rinsed twice with deionized distilled water prior to use. When laminin was used with collagen IV, collagen IV was prepared as described, and laminin was subsequently added In the usual manner. Matrigel (Collaborative Research) was utilized according to manufacturer's instructions.

Primary cultures were prepared as describe above and plated onto a number of different substrates and examined by phase contrast as well as immunofluorescence with antivimentin antisera (FIG. 6). Cells maintained on lainthin (FIG. 6A and B) resemble those grown on fibronectin (6D and E), though the processes are shorter with the latter substrate. Combining laminin and fibronectin (FIGS. 6E and F) provides an appearance similar to laminin alone. Cells maintained on poly-D-lysine (FIGS. 6G and H) display poor plating efficiency and minimal process outgrowth, while with polyornithine (FIGS. 6I and J) they appear only slightly better than with poly-D-lysine. Laminin and polyornithine together (FIGS. 6K and L) afford better plating efficiency and neurite outgrowth, which remains inferior to laminin or fibronectin. Heparan-sulfate (FIGS. 6M and N) yields similar results to polyornithine. Although collagen (FIGS. 6O and P) allows somewhat better plating efficiency than poly-D-lysine, polyornithine or heparan-sulfate, process outgrowth is still stunted and plating efficiency is not optimal. Collagen IV (FIGS. 6Q and R) yields improved neurite outgrowth and plating efficiency, which is still inferior to fibronectin or laminin. Utilization of laminin and collagen IV together (FIGS. 6S and T) yields better plating efficiency and neurite outgrowth, which is inferior to laminin or fibronectin. Thus, of all substrates tested, laminin consistently provides optimal plating efficiency and therefore, has been used for subsequent experimentation.

Figure 7A:
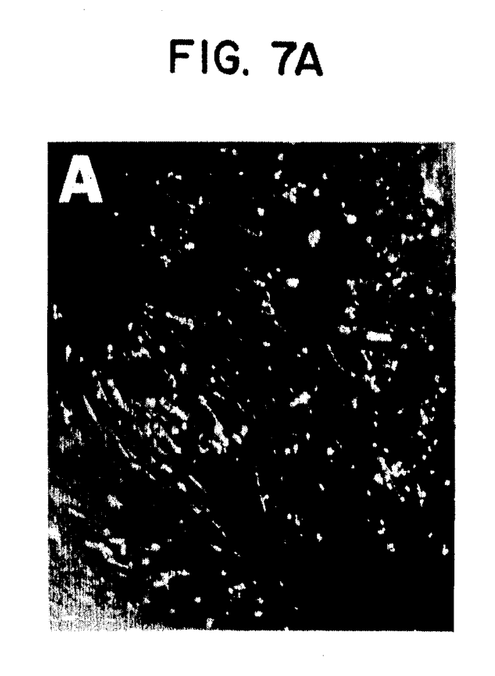
FIG. 7A, laminin.
Figure 7B:
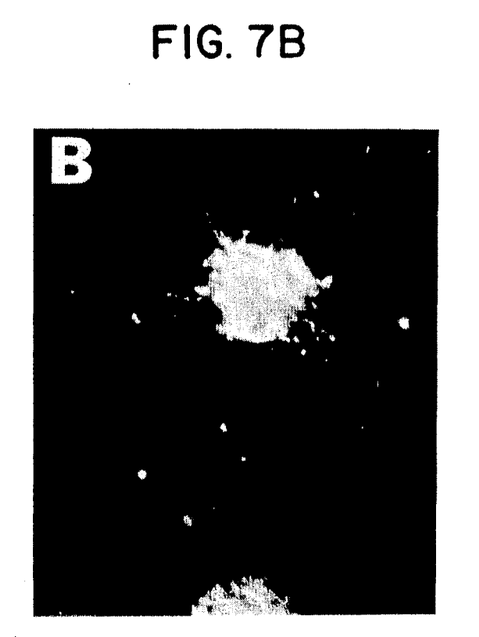
FIG. 7B, matrigel.
Figure 7C:
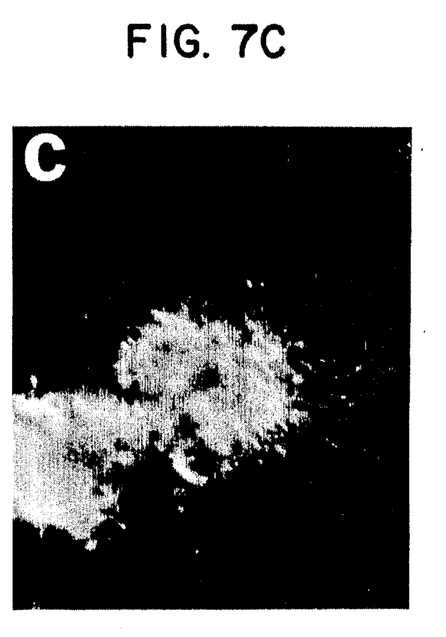
FIG. 7C matrigel at higher magnification.

Matrigel was also examined as a substrate (FIG. 7). On laminin, cells extend neurites in a random fashion, with no tendency to reaggregate (FIG. 7A). By contrast, when duplicate suspensions of cells are plated onto matrigel, the cells aggregate over the next 48 hr to form clusters (FIGS. 7B and C). Some cells extend perpendicularly from these clusters, with the extending process demonstrating multiple short, branched processes. Thus, in a three dimensional matrix, these culture cells assume a polarity, with structures representing putative cilia extending apically.

EXAMPLE 5

This example describes the role of NGF in maintaining olfactory neuronal cells in culture.

Figure 8A:
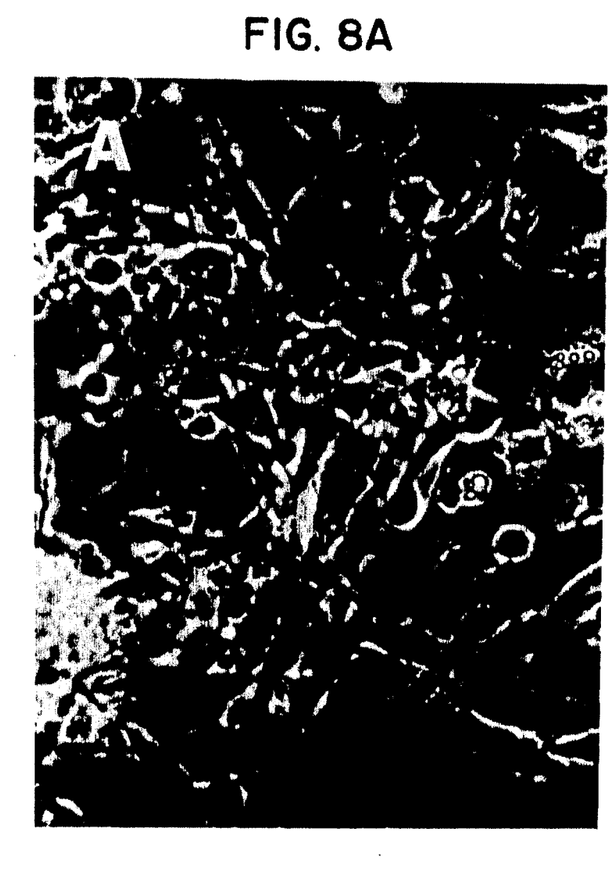
Figure 8B:
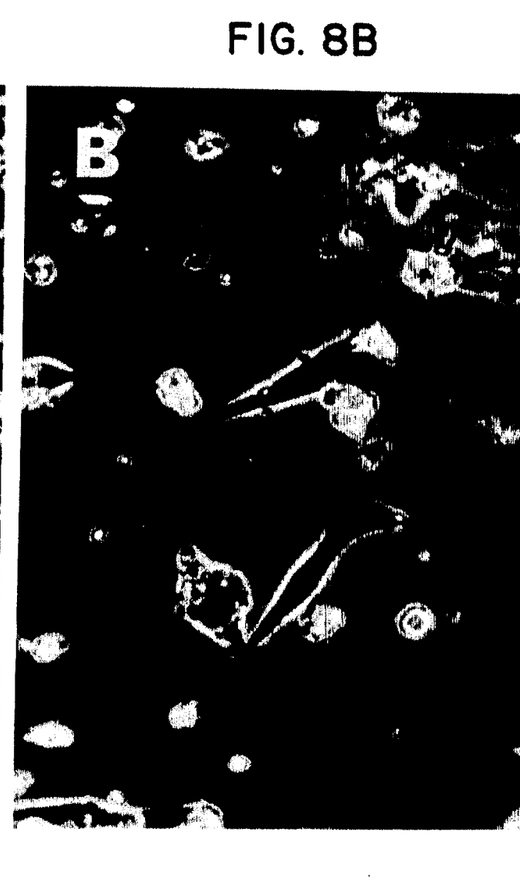

NGF is thought to play an important role in neuronal maturation and differentiation (for review, see Levi et al., (1988) Misko, Radeke et al., (1987) *J. Exp. Biol.*, 132:177–190. To investigate the role of NGF on olfactory neuronal survival and neurite extension, primary cultures were plated in the absence or presence of NGF at concentrations of 25 ng/ml (FIG. 8). Primary cultures were plated into two-chamber slides. An aliquot of medium with (FIG. 8A) or without (FIG. 8B) NGF was added after cells were plated. Although both sets of cells initially extend processes with good plating efficiency, by 3 days in culture those cells maintained without NGF lose process extension and cell viability is decreased by approximately 85%. Therefore, NGF apparently affects both olfactory neuronal survival and neurite extension in culture.

EXAMPLE 6

This example describes the excitation of primary olfactory neuron cultures by odorants.

After 5–7 days in primary culture, olfactory neuronal cells were exposed to odorants and cyclic AMP levels assayed. To avoid transient changes in intracellular cyclic AMP levels caused by feeding, the medium was changed to 0.5 ml of MEM-AIR containing 0.1% (w/v) RIA-grade BSA 2–3 hr before use. At zero-time, cultures received an additional 0.5 ml of MEM-AIR with or without 10 uM 2-isobutyl-3-methoxypyrazine (IBMP). At various times thereafter the entire medium was aspirated and the reaction quenched by addition of 6% in cold TCA. Cellular extracts were processed and RIA for cyclic AMP was performed as described below.

Primary cultures of olfactory neurons were plated in laminin-treated 24-well cluster dishes at a density of $1 \times 10^6$ cells per $cm^2$. Cells were used between days 5–7 in culture. Thirty min before experimentation, monolayers were fed with MEM-AIR containing 0.1% (w/v) RIA grade BSA. Immediately prior to use, odorants were diluted from a 450 mM stock in absolute ethanol to 10 uM. At zero time, 0.5 ml of MEM-AIR containing 0.1% RIA grade BSA and odorant at twice the final concentration was added to wells.

The experiment was terminated by aspiration of culture medium and addition of 200 ul of 6% (w/v) trichloroacetic acid (TCA) at 0° C. Culture wells were heated to 56° C. in an oven for 1 hr, scraped, sonicated, chilled, and microfuged for 30 sec. The supernatants were extracted 4 times with 5 volumes of ether, and the ether-extracted water phase was lyophilized to dryness. Samples were resuspended in 200 ul of RIA-NEN buffer (NEN/DuPont, Boston, MA) and RIA assay was performed according to specifications of the cyclic AMP kit.

TABLE 1

Effect of Odorant on cAMP Levels in Culture Cells

| | cAMP (% of control ± SEM) |
|---|---|
| Primary olfactory neurons time (min) | |
| 0.5 | 350 ± 160 |
| 1.0 | 250 ± 92 |
| 5.0 | 270 ± 113 |
| 15 | 175 ± 47 |
| NG-108 cells time (min) | |
| 0.5 | 103 ± 19 |
| 1.0 | 94 ± 32 |
| 5.0 | 99 ± 16 |
| 15 | 70 ± 41 |

IBMP elicits a rapid, transient rise in intracellular cyclic AMP levels (Table 1). The maximum increase seen is approximately three-fold over control levels. Similar treatment of NG-108 cells does not alter cyclic AMP levels.[1]

[1] NG-108 cells (a generous gift from Dr. Karen Braas, University of Vermont, Burlington, Vt.) were grown and maintained as previously described (Braas, Childers and U'Prichard, 1983). For experimentation, cells were plated in 24-well clustered dishes and treated similarly to olfactory neurons. NG-108 cells are hybrid cells of a globlastoma and a non-olfactory neural-like cell. NG-108 is a continuous cell line.

We claim:

1. A primary culture of dissociated olfactory neurons, wherein said olfactory neurons comprise at least about 85% of all cells in said primary culture, said neurons demonstrating responsiveness in culture to 1 nM IBMP, to between about 1 and about 10 uM citralva, and to between about 1 and about 10 uM isovaleric acid, said neurons expressing vimentin, olfactory marker protein and neuron-specific enolase, said neutrons not expressing glial fibrillary acidic protein, S-100 protein, keratin, or neurofilament protein, said expression being assessed by immunohistochemistry or by Western blotting.

2. The primary culture of claim 1 wherein the olfactory neurons comprise at least about 90% of the cells in the culture.

3. The primary culture of claim 1 wherein the neurons are mammalian.

4. The primary culture of claim 1 wherein the neurons are from a rat.

5. The primary culture of claim 1 wherein the neurons are neonatal.

* * * * *